(12) United States Patent
Heilek et al.

(10) Patent No.: US 7,947,845 B2
(45) Date of Patent: May 24, 2011

(54) PROCESS FOR PURIFYING REMOVAL OF ACRYLIC ACID, METHACRYLIC ACID N-VINYLPYRROLIDONE OR P-XYLENE CRYSTALS FROM THEIR SUSPENSION IN MOTHER LIQUOR

(75) Inventors: Joerg Heilek, Bammental (DE); Ulrich Hammon, Mannheim (DE); Klaus Joachim Mueller-Engel, Stutensee (DE); Dieter Baumann, Speyer (DE)

(73) Assignee: BASF SE, Ludwigshafen (DE)

( * ) Notice: Subject to any disclaimer, the term of this patent is extended or adjusted under 35 U.S.C. 154(b) by 304 days.

(21) Appl. No.: 12/170,002

(22) Filed: Jul. 9, 2008

(65) Prior Publication Data

US 2009/0018347 A1 Jan. 15, 2009

Related U.S. Application Data

(60) Provisional application No. 60/949,056, filed on Jul. 11, 2007.

(30) Foreign Application Priority Data

Jul. 11, 2007 (DE) .......... 10 2007 032 633

(51) Int. Cl.
C07D 207/267 (2006.01)
(52) U.S. Cl. ........... 548/555; 562/600
(58) Field of Classification Search .......... 562/600; 548/555

See application file for complete search history.

(56) References Cited

U.S. PATENT DOCUMENTS

| 4,481,169 | A | 11/1984 | van der Malen |
| 5,537,832 | A | 7/1996 | Keus |
| 7,540,884 | B2 * | 6/2009 | Hammon et al. ........... 23/295 R |
| 7,762,404 | B2 * | 7/2010 | Heilek et al. ........... 210/456 |
| 2004/0116741 | A1 | 6/2004 | Nordhoff et al. |
| 2004/0256319 | A1 | 12/2004 | Hammon et al. |
| 2005/0006299 | A1 | 1/2005 | Heilek et al. |
| 2005/0222459 | A1 | 10/2005 | Nordhoff et al. |

FOREIGN PATENT DOCUMENTS

| DE | 101 49 353 A1 | 7/2002 |
| DE | 102 11 686 A1 | 10/2003 |
| EP | 0 098 637 A1 | 1/1984 |
| WO | WO 03/041832 A1 | 5/2003 |
| WO | WO 03/041833 A1 | 5/2003 |

OTHER PUBLICATIONS

P.J. Jansens, et al., "The Purification Process in Hydraulic Packed-Bed Wash Columns", Chemical Engineering Science, Elsevier Science Ltd., vol. 50, No. 17, 1995, pp. 2717-2729.

D. Verdoes, et al., "Improved Procedures for Separating Crystals from the Melt", Applied Thermal Engineering, Verlag Elsevier Science Ltd., vol. 17, No. 8-10, 1997, pp. 879-888.

European Search Report dated Aug. 3, 2010, in the corresponding Belgium Application No. BE200800380 (submitted with with English translation of categories).

* cited by examiner

*Primary Examiner* — Rei-tsang Shiao

(74) *Attorney, Agent, or Firm* — Oblon, Spivak, McClelland, Maier & Neustadt, L.L.P.

(57) ABSTRACT

A process for purifying removal of acrylic acid, methacrylic acid, N-vinylpyrrolidone or p-xylene crystals from their suspension in mother liquor by means of a wash column with forced transport, whose shell of the process chamber is a metal wall, the wash column additionally being enveloped by a thermal insulation material having a water vapor barrier and a specific heat flow of $>0.1$ W/m$^2$ and $<10$ W/m$^2$ flowing into the process chamber through the metal wall of the wash column.

13 Claims, 5 Drawing Sheets

US 7,947,845 B2

PROCESS FOR PURIFYING REMOVAL OF ACRYLIC ACID, METHACRYLIC ACID N-VINYLPYRROLIDONE OR P-XYLENE CRYSTALS FROM THEIR SUSPENSION IN MOTHER LIQUOR

CROSS-REFERENCE TO RELATED APPLICATIONS

This application claims priority to U.S. Provisional Application No. 60/949,056, filed Jul. 11, 2007 and to German Application No. 10 2007 032 633.7, filed Jul. 11, 2007.

BRIEF SUMMARY OF THE INVENTION

The present invention relates to a process for purifying removal of acrylic acid, methacrylic acid, N-vinylpyrrolidone or p-xylene crystals from their suspension in mother liquor, in which the suspension is fed to a wash column which has a metal wall which encloses a process chamber, mother liquor is released from the process chamber while retaining the crystals to form a crystal bed in the process chamber from the suspension conducted into the process chamber, the crystal bed is conveyed within the process chamber, at least one force other than gravity acts in the process chamber in the conveying direction of the crystal bed and conveys the crystal bed within the process chamber, pure melt which consists of molten crystals which have been removed in a purifying manner by the process claimed is conducted within the process chamber in countercurrent to the crystal bed such that a wash front which divides the crystal bed into a mother liquor zone and into a pure melt zone forms in the crystal bed, and a specific heat flow flows through the metal wall of the wash column (from the outside) into the process chamber of the wash column.

In this document, the term "mother liquor" shall be understood such that it comprises melts of the compounds to be crystallized and impurities and/or solutions of the compounds to be crystallized and solvents (or solvent mixtures) and impurities.

Numerical addresses in this document always relate to figures appended to this document.

The process according to the preamble of this document is known (cf, for example, WO 03/041832 and WO 03/041833).

BACKGROUND OF THE INVENTION

It generally follows a suspension crystallization, which is a very effective and inexpensive process for achieving a high purity of a desired chemical compound. What is utilized here is the fact that impurities are substantially displaced from the crystal lattice and remain in the mother liquor as crystals grow in a liquid. Even in a one-stage crystallization process, highly pure crystals of the desired compound are therefore obtained. If required, the suspension crystallization can be performed in several stages.

A crucial step which has a critical influence on the purity of the crystallized target product is the removal of the highly pure crystals from their mother liquor, which comprises the impurities in enriched form and the uncrystallized fractions of the target product, by a solid/liquid separation process. This separation process can proceed in a plurality of stages, and a so-called wash column is often used at least in the last stage. However, the wash column may also be the only separating stage. It essentially has the task of separating the comparatively pure crystal phase from the comparatively contaminated mother liquor.

Wash columns are likewise known from the aforementioned prior art. They comprise a generally cylindrical wall which delimits a process chamber. Frequently connected upstream of the process chamber is a distributor chamber, into which the crystal suspension to be separated in the wash column is fed. On its way from the distributor chamber into the process chamber, the crystal suspension is distributed substantially uniformly over the cross section of the process chamber. In the process chamber, a relatively dense crystal bed is obtained by mother liquor withdrawal and is conveyed through the process chamber (this can be done from the top downward or from the bottom upward). A melt of the molten crystals themselves is passed through the crystal bed in countercurrent as wash liquid.

For the formation of a crystal bed, different methods are useful in principle. In wash columns which work with gravity, the crystal suspension is introduced into the column from the top, the crystal bed forms in a sedimentation process and it is conveyed in the conveying direction only through the action of gravity.

The use of such columns is excluded from the process according to the invention, since generally no defined wash front is formed therein, especially when they are provided with a stirrer for part of their height (cf. FIG. 1).

The process according to the invention is accordingly restricted to processes in wash columns with forced conveying of the crystal bed (a comprehensive description of the different wash column types can be found, inter alia, in Chem.-Ing.-Techn. 57 (1985) No. 291-102, in Chemical Engineering Science Vol. 50, No. 17, p. 2712 to 2729, 1995, Elsevier Science Ltd., in Applied Thermal Engineering Vol. 17, No. 8-10, p. 879-888, 1997, Verlag Elsevier Science Ltd., and in the literature cited in the aforementioned literature references and also in DE-A 102 45 164, DE-A 102 11 686, DE-A 101 49 353, WO 03/041832 and WO 03/041833).

In wash columns with forced transport (or conveying) of the crystal bed, a conveying force other than gravity acts in the conveying direction (or transport direction) of the crystal bed.

In principle, wash columns with forced transport of the crystal bed are divided into pressure columns (also known as hydraulic wash columns or hydraulic columns) and into mechanical columns. In the case of the pressure columns, the crystal suspension is conveyed into a wash column under pressure (for example by pumping and/or hydrostatic head). The liquid flow imposed by the feed column pressure then ensures compaction of the crystals to a crystal bed (cf. FIG. 2) and its conveying (the hydraulic pressure is typically from 0.1 to 10 bar, frequently from 1 to 5 bar). The mother liquor generally flows out of the wash column through filters (beyond the filter, the pressure may be standard pressure, reduced pressure or superatmospheric pressure). The recycling of a portion of the mother liquor enables the control of the transport force (control stream).

In contrast, mechanical wash columns comprise a mechanical forced conveying device for the crystals. In the simplest case, this may be a semipermeable plunger which is permeable to the mother liquor but impermeable to the crystals in the suspension supplied (cf. FIG. 3) and through whose shifting the pressure to densify and convey the crystal bed is generated.

The densification to a crystal bed and its conveying can, though, also be effected by removing the mother liquor through filters and mechanically transporting the crystals from the filter to the crystal bed by means of a rotating conveying element (for example screws, stirrers, helices or spirals) (cf. FIG. 4). The filters may also be integrated into the rotating conveying elements. Beyond the mother liquor outlet, the pressure here too may again be standard pressure, reduced pressure or superatmospheric pressure.

The crystal bed in the wash columns with forced transport of the crystal bed to be used in accordance with the invention has a so-called buildup front at which crystals of the crystal suspension introduced continuously add on. The buildup front thus indicates the transition from the suspension to the crystal bed and is characterized by a relatively abrupt rise in the crystal content in the suspension. In hydraulic wash columns, this buildup front is also referred to as the filtration front.

At the opposite end of the crystal bed to the buildup front, a kind of rotor blade (for example slotted rotating knife blade) or scraper is usually arranged, which continuously removes crystals from the crystal bed. The continuous addition of crystals at the buildup front on the one hand and the continuous removal of crystals at the opposite end of the crystal bed to the buildup front on the other hand defines the transport direction of the crystal bed (it may either point from the top downward or from the bottom upward). The crystals removed from the crystal bed are, if appropriate after they have been resuspended in pure melt, melted by heat transfer. A portion of the melt is removed as pure product stream and another portion of the pure melt is recycled as wash liquid against the transport direction of the crystal bed at its opposite end to the buildup front into the process chamber. Typically, the wash liquid is at melting point temperature.

The melting of a portion of the crystals can, though, also be undertaken immediately within the wash column (for example by means of corresponding installed apparatus for heating at the opposite end of the process chamber to the buildup front).

In that case, likewise only a portion of the melt obtained is withdrawn from the column. The other portion rises as wash melt.

The conveying of the pure melt in the opposite direction to the conveying direction of the crystal bed virtually forces the crystal bed saturated with mother liquor into the pure melt, and the mother liquor is in fact forced back to a certain degree by the pure melt within the crystal bed.

In the steady state, the result of this process is a wash front at a defined height in the crystal bed, which is defined as that point in the process chamber in the wash column where the highest temperature and concentration gradients occur (i.e., in the wash front, the temperature, for example, jumps, above and below the wash front, essentially constant temperatures are present). Roughly speaking, pure melt and mother liquor adjoin in the wash front. The region from the wash front to the buildup front is referred to as the mother liquor zone and the region from the wash front up to the opposite end of the crystal bed from the buildup front is referred to as the pure melt zone. The position of the wash front can be adjusted by controlling transported mass flow rate of crystals and opposing pure melt flow rate. It is frequently the case that the washing action becomes better with increasing length of the pure melt zone. Normally, the wash front has a longitudinal dimension (at right angles to the cross section of the wash column) of $\leq 100$ mm, generally $\leq 60$ mm and usually $\leq 40$ mm. The latter longitudinal dimensions apply especially when the crystal bed, in contrast to EP-A 098 637, is completely unstirred. The cross section of the process chamber of the wash column may be circular, oval or angular (for example regular polygonal).

As the material for the wall delimiting the process chamber of the wash column, WO 03/041832 recommends the use of metal. The metals used may, according to the substance to be purified, be metals of different kinds. The metals may be pure metals or else alloys, for example carbon steels, iron-base alloys (stainless steel, for example with Cr/Ni addition) or nickel-base alloys (e.g. Hastelloy qualities). When the crystals to be removed in a purifying manner are those of acrylic acid (when acrylic acid is the target product), the preferred wall material of the wash column is stainless steel, especially stainless steel of DIN material No. 1.4571 or 1.4541, or stainless steel similar to these stainless steels with regard to the alloy elements. The thickness of the metal wall delimiting the process chamber is appropriately from 3 to 30 mm, frequently from 4 to 20 mm and usually from 5 to 15 mm, especially in the case of stainless steel.

A disadvantage of using metal as the material for the wall delimiting the process chamber of the wash column is, however, the high thermal conductivity of metals (at 300 K, the thermal conductivity of unalloyed steel is, for example, 50 W/m·K, that of stainless steel 21 W/m·K and that of aluminum 237 W/m·K, while the corresponding thermal conductivity of glass is only 1.0 W/m·K).

The aforementioned is disadvantageous in that the melting point of a pure substance is at a higher temperature than the melting point of the same substance but comprising impurities (freezing point depression). The consequence of this fact is that the temperature in the mother liquor is normally below the temperature in the pure melt zone. According to the impurity content of the mother liquor, this temperature difference can be up to 15° C. and more, frequently from 4 to 10° C. and, in the case of only a low impurity content of the mother liquor, from 2 to 4° C.

Owing to the high thermal conductivity of metals, this leads to the fact that heat is removed through the metal wall surrounding the process chamber from the pure melt zone at a higher temperature to the mother liquor zone at a lower temperature. The result may be undesired crystallization over the length of the pure melt zone on the side of the metal wall facing toward the process chamber, which reduces the throughput through the wash column owing to increased frictional losses or increases the pressure drop.

As a remedy, WO 03/041832 recommends introducing a controlled specific heat flow from the outside through the metal wall into the process chamber of the wash column at least over the length of the pure melt zone, specific heat flows of from 10 to 50 W/m² being recommended as very particularly preferred.

As a realization of such a heat flow input which is particularly favorable from an application point of view, WO 03/041832 recommends surrounding the wash column as such with an outer housing and keeping the air present between outer housing (which is permeable to the ambient air) and metal wall at a temperature above the temperature of the melting point of the pure melt withdrawn from the wash column by means of heating. The difference between the two temperatures may be up to 20° C. or more.

In the case of acrylic acid, methacrylic acid, N-vinylpyrrolidone or p-xylene crystals, such a procedure has, however, been found to be disadvantageous, since, according to D'ANS•LAX, Taschenbuch für Chemiker und Physiker [Handbook for Chemists and Physicists], Springer-Verlag, Berlin 1964, Vol. II, Organische Verbindungen [Organic Compounds], the melting points of the aforementioned compounds as a pure substance are in the range from 12 to 16° C.

In other words, the temperature of the suspension in which the crystals of the aforementioned relevant compounds normally occur in the corresponding suspension crystallization (and hence the temperature of the mother liquor zone in the wash column) will generally be ≦10° C., and the temperature of the ambient air present in the outer housing will typically be ≧17° C.

This is disadvantageous in that, for example, the dew point of air at a temperature of 18° C. and a relative air humidity of 85% is 15.4° C. (even in the case of a relative air humidity of the aforementioned air at 18° C. of only 65%, its dew point at 11.3° C. is still above 10° C.). In the case of a relative air humidity of 95% of the air at 18° C., its dew point is 17.2° C. At an air temperature of 15° C. and a relative air humidity thereof of 95% (75%), its dew point is still 14.2° C. (10.6° C.).

The relative air humidity specifies how many percent of the maximum possible water vapor content at the particular temperature the air comprises. The dew point temperature (the dew point) is defined as the temperature at which the current water vapor content in the air is the maximum (100% relative air humidity). In other words, when the temperature goes below the dew point temperature (the dew point), a portion of the water vapor present in the air condenses out.

Therefore, when the described recommendation of WO 03/041832 is followed, water vapor will generally condense out of the ambient air on the metallic outer surface of the wash column at least in the region of the mother liquor zone. Such condensate formation is disadvantageous for various reasons. Firstly, condensate dripping off the wash column is capable of undesirably simulating leakage of the wash column. Secondly, the aqueous condensate can lead in an undesired manner to corrosion phenomena (for example regarding the drive of the rotor blade for the continuous removal of the crystal bed), and the heat of condensation released in the condensation can finally impair the homogeneity of operation of the wash column.

DETAILED DESCRIPTION OF THE INVENTION

Figure 1:
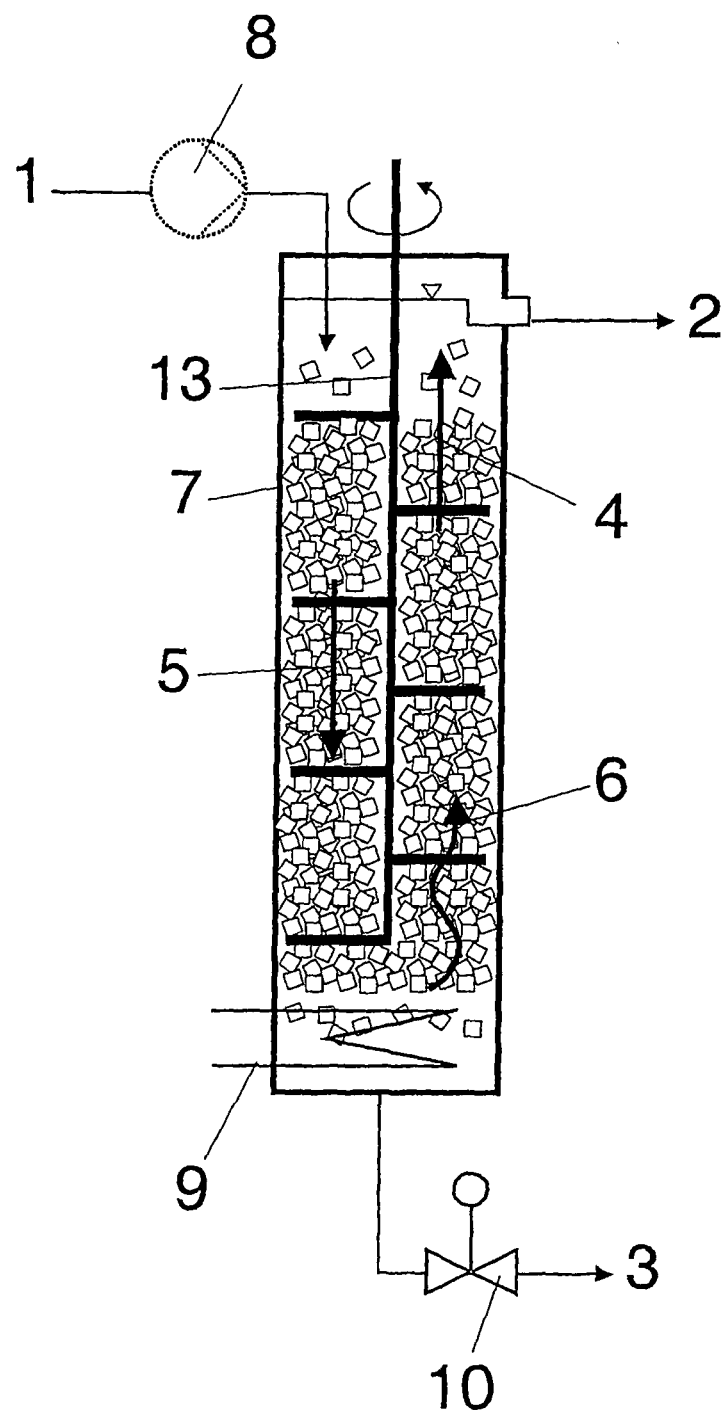
FIG. 1: Wash columns which work with gravity, the crystal suspension is introduced into the column from the top, the crystal bed forms in a sedimentation process and it is conveyed in the conveying direction only through the action of gravity.
Figure 2:
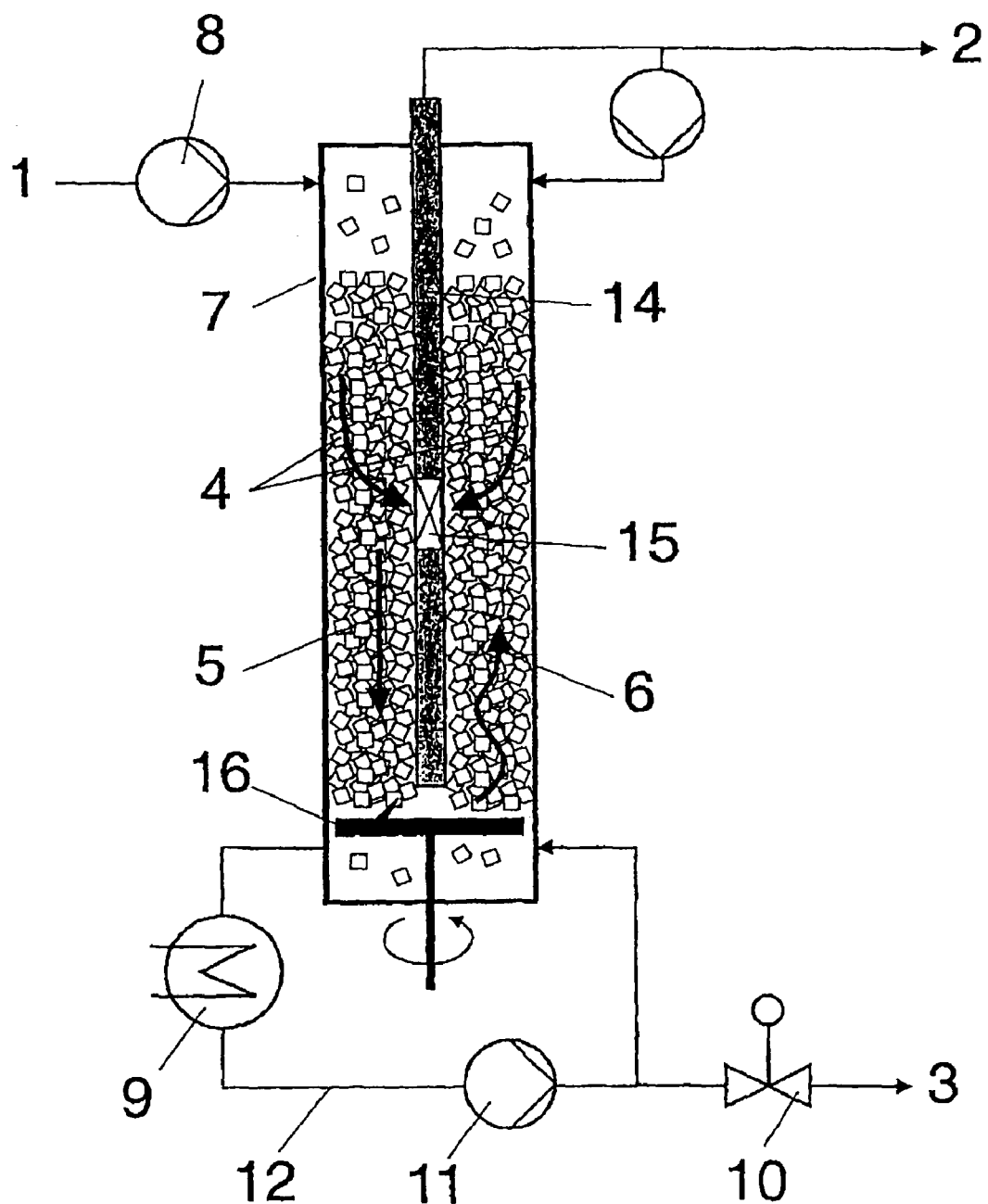
FIG. 2: Liquid flow imposed by the feed column pressure.
Figure 3:
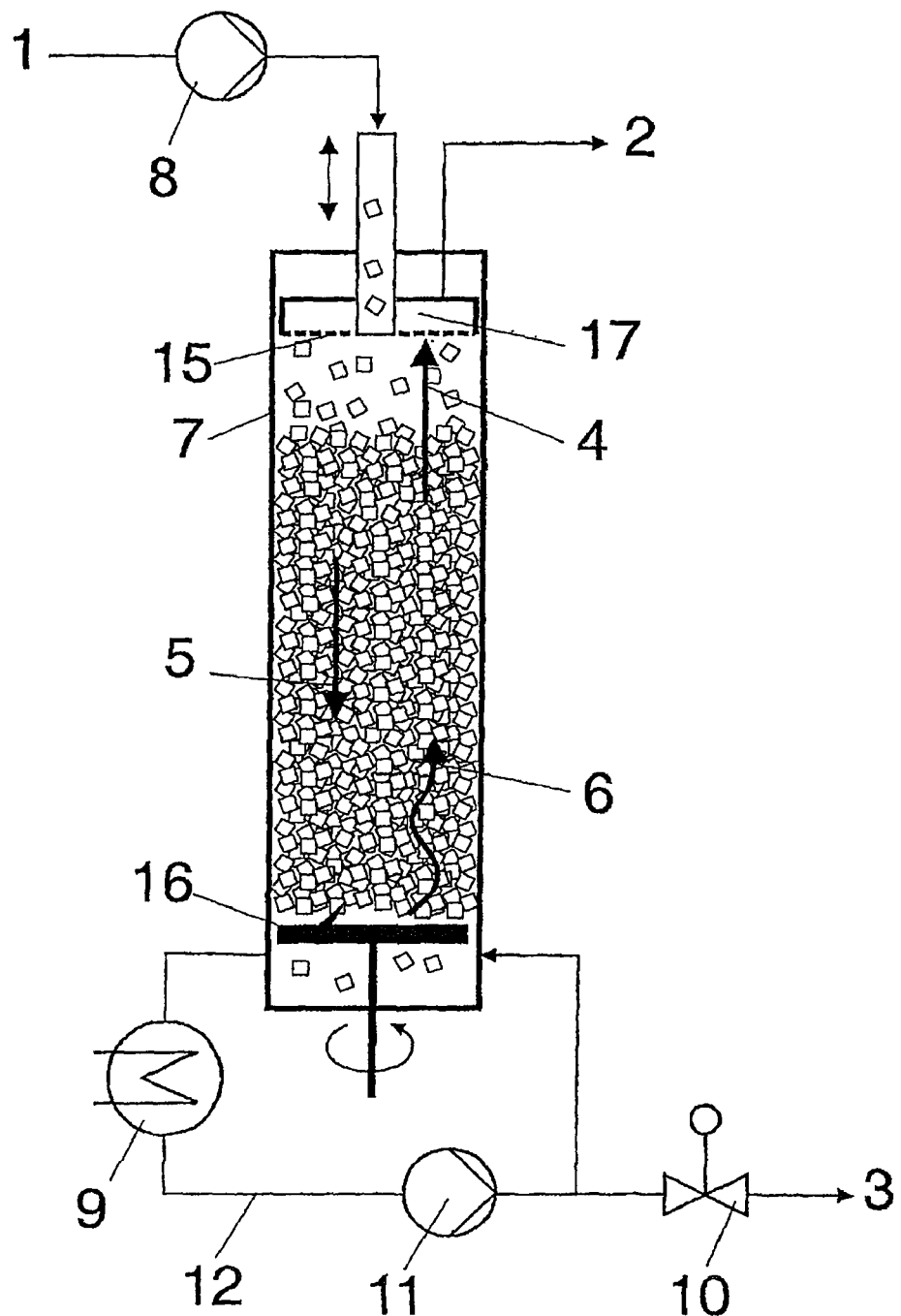
FIG. 3: Mechanical wash columns comprising a mechanical forced conveying device for the crystals.
Figure 4:
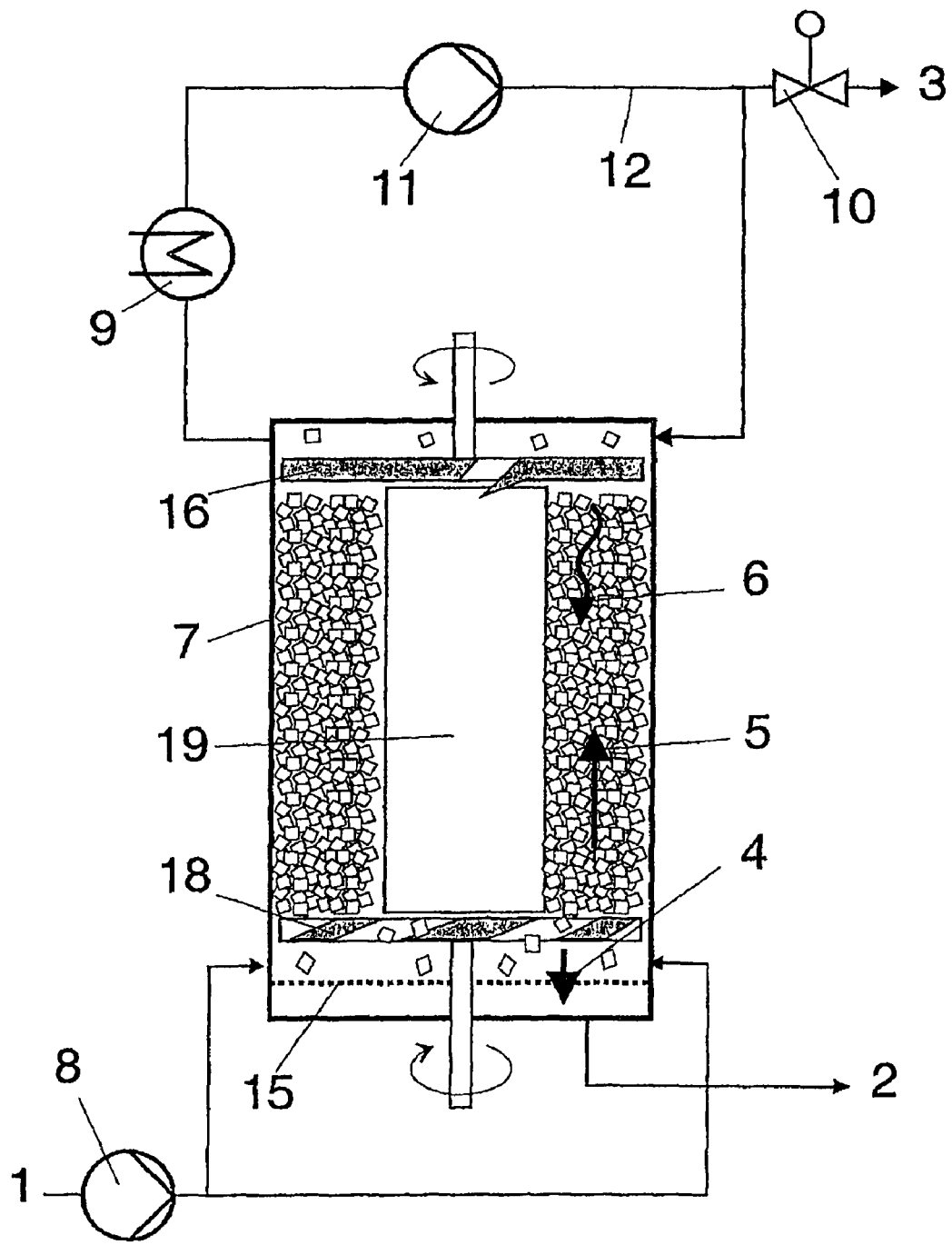
FIG. 4: The densification to a crystal bed and its conveying by removing the mother liquor through filters and mechanically transporting the crystals from the filter to the crystal bed by means of a rotating conveying element.

It was therefore an object of the present invention to improve the procedure recommended in the prior art.

Accordingly, a process has been found for purifying removal of acrylic acid, methacrylic acid, N-vinylpyrrolidone or p-xylene crystals from their suspension in mother liquor, in which the suspension is fed to a wash column which has a metal wall which encloses a process chamber,
mother liquor is released from the process chamber while retaining the crystals to form a crystal bed in the process chamber from the suspension conducted into the process chamber,
the crystal bed is conveyed within the process chamber,
at least one force other than gravity acts in the process chamber in the conveying direction of the crystal bed and conveys the crystal bed within the process chamber,
pure melt which consists of molten crystals which have been removed in a purifying manner by the process claimed is conducted within the process chamber in countercurrent to the crystal bed such that a wash front which divides the crystal bed into a mother liquor zone and into a pure melt zone forms in the crystal bed, and
a specific heat flow flows through the metal wall of the wash column (from the outside) into the process chamber of the wash column, wherein the metal wall of the wash column which encloses the process chamber is itself enclosed by a shell of a thermal insulation material, with the proviso that the shell composed of the thermal insulation material has a water vapor barrier whose environment facing away from the process chamber is permeable to the ambient air and whose surface facing away from the process chamber has a temperature which is above the dew point (above the dew point temperature) of the ambient air, and the specific heat flow flowing into the process chamber of the wash column through its metal wall is >0.1 W/m$^2$ and <10 W/m$^2$.

Preferably in accordance with the invention, the specific heat flow flowing into the process chamber of the wash column through its metal wall is from ≧1 (or ≧2) to ≦9 W/m$^2$, advantageously from ≧3 to ≦8 W/m$^2$ and most preferably from ≧4 to ≦7 W/m$^2$.

Surprisingly, heat flows of the aforementioned magnitudes are sufficient to counteract the undesired crystal formation, addressed in WO 03/041832, on the side of the metal wall facing the process chamber along the pure melt zone to a sufficient degree.

This is especially true when the temperature difference between mother liquor zone and pure melt zone is from 3 to 12° C., or from 4 to 10° C. or from 3 to 8° C.

Useful metals for the wall surrounding the process chamber include all metals already named in this document and all of those named in WO 03/041832, including the wall thicknesses mentioned there.

Useful thermal insulation materials are in principle all materials whose thermal conductivity λ (W/m·K) is lower than that of the metal selected for the metal wall enclosing the process chamber (frequently, λ is also referred to as the coefficient of thermal conductivity, thermal conductivity number or specific thermal conductivity).

Advantageously in accordance with the invention, the thermal insulation materials used for the shell of the wash column are those whose thermal conductivity λ (W/m·K)≦0.3 W/m·K, preferably ≦0.1 W/m·K, more preferably ≦0.08 W/m·K and even more preferably ≦0.06 and in many cases even ≦0.04 or ≦0.02 or ≦0.01 W/m·K (in each case based on a temperature of 300K). In general, the thermal conductivity λ of thermal insulation materials to be used in accordance with the invention at 300° C. is, however, at values of ≧0.001 W/m·K, frequently even at values of ≧0.002 W/m·K.

Examples of useful such thermal insulation materials include: wood, wood wool, fiber mats made from Chinese silvergrass, poroton, mineral wool (e.g. glass wool), foam glass, polystyrene insulating materials such as the expanded polystyrenes Styropor®, Styrodur® and Neopor® (additionally comprises fine graphite particles), polyurethane insulating materials such as rigid polyurethane foam, carbon dioxide-PUR, c-iso-pentane-PUR, fumed silica (for example pressed plates thereof), evacuated PUR and evacuated silica.

In a particularly simple manner from an application point of view, the thermal insulation material can be applied directly to the metal wall of the wash column (for example Styropor in a thickness of from 40 to 80 mm). The shell may be manufactured from individual thermal insulation material pieces (e.g. Styropor pieces) joined together to form the overall shell. The securing on the metal surface of the wash column is preferably effected mechanically (particularly appropriate from an application point of view is fixing with the aid of metal wire (for example of stainless steel) or with the aid of steel tensioning belts).

Instead of applying the thermal insulation material directly to the metal surface of the wash column, it is also possible, for example, to deliberately leave an air cushion between the metal surface and the actual thermal insulation material. In this case, the overall thermal insulation material which encloses the wash column consists of two layers: an inner air layer facing toward the metal surface of the wash column (the process chamber of the wash column) and an outer layer composed of the actual thermal insulation material. In principle, useful thermal insulation materials for the process according to the invention are also composite thermal insulation substances consisting of a plurality of successive layers of different materials.

An integral constituent of the thermal insulation material enclosing (enveloping) the wash column is, necessarily in accordance with the invention, a water vapor barrier (often also referred to as a water vapor diffusion barrier). In this document, according to ISO 9229, this is understood to mean a layer which essentially prevents the continuous diffusion of water vapor present in the ambient air onto the surface of the metal wall of the wash column directed away from the process chamber of the wash column.

In principle, the water vapor barrier may be a relatively thin layer of material essentially impermeable to water vapor, which can be applied (for example adhesive-bonded), for example, in a simple manner onto the surface (exterior) of the actual thermal insulation material facing away from the process chamber. What is formed in this way is again a composite thermal insulation substance from which the inventive shell of the wash column is formed.

Useful such materials include especially those which have a high water vapor diffusion resistance number $\mu$. This is a dimensionless material characteristic which specifies the factor by which the material in question is more impervious to water vapor than an air layer of equal thickness at rest. It is determined on the basis of DIN EN ISO 7783 (1-2) and DIN EN ISO 12572.

To obtain a water vapor barrier layer, useful materials for the process according to the invention are especially those whose water vapor diffusion resistance number is $\geq 5000$, preferably $\geq 10000$ and more preferably $\geq 15000$, even better $\geq 50000$, or $\geq 100000$, or $\geq 1000000$ or $\geq 10000000$.

This is because such materials enable, even in the case of a comparatively low layer thickness, a water vapor barrier action which is entirely satisfactory in the sense of the invention. A measure employed for the water vapor barrier action is typically the product $sd=\mu \cdot x$ where x is the layer thickness in "meters". The product sd is also referred to as the water vapor diffusion-equivalent air layer thickness. It specifies the thickness of that air layer in meters which offers the same resistance to diffusion of water vapor through it as an air layer sd at rest in "meters".

Water vapor barrier layers with an sd of $\geq 500$ m, preferably $\geq 1000$ m, and more preferably $\geq 1500$ m or most preferably $\geq 30000$ m are preferred in accordance with the invention.

Frequently, water vapor barrier layers to be used in accordance with the invention are manufactured from polyolefins (e.g. polyethylene). The $\mu$ value of polyethylene films is typically 500000. In other words, a 2 mm-thick polyethylene coating has an sd value of 1000 m.

For the process according to the invention, the water vapor barrier layers used are, however, metal foils. Their $\mu$ values are generally above 10000000 (e.g. Al, $\mu$=30 000 000). In other words, layer thicknesses of less than 1 mm (in the case of Al, for example, 0.05 mm) are generally sufficient to achieve an sd value of 1500 m which, according to DIN 4108, has "water vapor imperviousness". Particularly preferred water vapor barrier layers are aluminum foils.

However, a disadvantage of metal foils is their low tearing resistance. In practice, metal composite foils are therefore used advantageously as water vapor barrier layers. These are foils in whose core a metal foil, for example an aluminum foil, is always present. The thickness of the metal foil is typically from 0.02 to 0.1 mm, in a manner particularly typical in accordance with the invention 0.05 mm. EP-A 1 090 969 and DE 299 17 320 U1 describe composite foils particularly suitable as water vapor barrier layers for the process according to the invention.

On the outside of the metal foil (for example of the Al foil), a layer of a base polymer is normally mounted. This base polymer assumes the protection of the sensitive metal foil and establishes the transition to the environment. This base material protects the metal foil (e.g. the Al foil) from mechanical damage, increases its tearing resistance (for example the tear propagation resistance) and additionally protects the metal foil from corrosion. In exceptional cases, the metal foil (e.g. the Al foil) can be protected on both sides by a polymeric layer. Useful base polymers include especially polyesters, polypropylene and polyamide. In the case of Al foils, polyethylene terephthalate is a preferred base polymer. Typically, the base polymer is adhesive-bonded to the metal foil with the aid of a lamination adhesive (for example a polyurethane dispersion). Typical layer thicknesses for the base polymer are from 0.01 to 0.02 mm.

A pressure-sensitive adhesive based on natural rubber, synthetic rubber or polyacrylate is generally applied on the side of the metal foil (e.g. aluminum foil) not protected by the base polymer and enables the metal composite foil to be adhesive-bonded to the actual thermal insulation material. Typical amounts of pressure-sensitive adhesive are approx. 40 g/m$^2$.

In order that the metal foil can firstly be rolled up for the purpose of saving storage space and secondly can be adhesive-bonded overlapping the substrate to be provided with the water vapor barrier layer, the base polymer has, on its side facing away from the aluminum film, advantageously so-called "controlled-release" siliconization. This ensures that, when release forces in the range from 1 N/cm to 3 N/cm are applied, the rolled-up metal composite film can be unrolled again without damage (cf. DIN EN 1939 and FINAT 10).

An example of a polymer-aluminum composite film outstandingly suitable for the inventive purposes is Terostat-Alu-Fixband from Teroson (Henkel). It has a water vapor diffusion resistance number $\mu$ of 600000 and an sd value of 900 m. Equally suitable for the inventive purposes is Alu-Butyl foil from WeGO Systembaustoffe, VTI branch in 67014 Ludwigshafen.

The latter comprises an aluminum foil of thickness 0.038 mm. The base polymer is polyethylene terephthalate of thickness 0.012 mm. It has been laminated onto the aluminum foil with the aid of an aqueous polyurethane adhesive dispersion. The pressure-sensitive adhesive applied to the reverse side of the aluminum foil is a synthetic butyl rubber (in a layer thickness of 0.6 mm). The pressure-sensitive adhesive in the case of this composite film is covered with a polyethylene film siliconized on one side, which enables the composite film to be rolled up without sticking, but has to be pulled off before the application as a water vapor barrier.

The aforementioned Alu-Butyl foil is commercially available with the standard dimensions 50 mm×10 m, 500 mm×10 m and 1000 mm×10 m. Preference is given to using the standard dimension 500 mm×10 m. In principle, it is also possible to adhesive-bond solely metal foil (e.g. aluminum foil) to the substrate to be modified with the water vapor barrier layer with the corresponding pressure-sensitive adhesive.

It will be appreciated that water vapor barrier films suitable in accordance with the invention may also be barriers consisting only of a plurality of polymer layers. Skilful combination of these individual polymers allows synergistic barrier potentials to be developed.

Instead of applying a water vapor barrier layer to the actual thermal insulation material, the water vapor barrier layer can also be incorporated into the thermal insulation material. This is the case, for example, when closed-cell thermal insulation substances are used.

When a water vapor barrier layer is applied to the actual thermal insulation material (for example aluminum composite foil onto polystyrene), it will be appreciated that it is possible to apply further heat insulation material to the water vapor barrier layer, so as to form a new overall thermal insulation material.

What is essential for the water vapor barrier and for the water vapor barrier layer is that, in the performance of the process according to the invention, it is positioned such that its surface facing away from the process chamber has a temperature which is above the dew point (above the dew point temperature) of the ambient air for which the environment of the water vapor barrier facing away from the process chamber is permeable.

In general, the thickness of water vapor barrier layers in the process according to the invention will vary within the range from 0.01 to 2 mm, in many cases within the range 0.025 to 1 mm. Its water vapor barrier action is, appropriately in accordance with the invention, such that its water vapor permeability is $\leqq 0.5$ g/m$^2$/day (e.g. 0.2 mm-thick polyethylene film), preferably $\leqq 0.4$ g/m$^2$/day, more preferably $\leqq 0.1$ g/m$^2$/day (e.g. aluminum composite films with a 0.05 mm-thick core of aluminum foil). Since the water vapor permeabilities are dependent directly on the outside atmosphere, the aforementioned values are based on a test climate of 20° C. with a relative air humidity of 85%. The testing is effected gravimetrically according to DIN 53122-1/DIN53122-A or according to ASTME-96 against air comprising an added desiccant.

In principle, it is also possible to test according to ISO 2528:1995 or according to DIN 53312-1/DIN 5312-A or according to DIN 53122-2/DIN 53122-2-A (the latter is an electrolysis process with a particularly low detection limit). Essentially, the different test methods differ in their sensitivity limit.

The wash column enclosed by a heat insulation material having a water vapor barrier (a water vapor barrier layer) can then be surrounded in an outer housing as such in such a manner as to be permeable to ambient air, and the air present between outer housing and the wash column enclosed in accordance with the invention (ambient air) can be kept at a temperature which ensures the heat flow required in accordance with the invention through the metal wall of the wash column into its process chamber by means of heating. Typically, for the purposes of the process according to the invention, a temperature difference between the temperature of the pure melt zone and the temperature of the ambient air in the outer housing of from $\geqq 2$ or $\geqq 5°$ C. to 20° C. or to 30° C. is sufficient (the ambient air has the higher temperature). The thermal insulation and the water vapor barrier are configured such that the dew point temperature plane for the ambient air, coming from the direction facing away from the process chamber of the wash column, is beyond the water vapor barrier (beyond the water vapor barrier layer).

The dew point temperature plane is that plane (if appropriate, for example, a cylindrical plane or a plane curved in another way) within the envelope (the enclosure) of the wash column (or the metal walls of its process chamber) in which the temperature corresponds to the dew point temperature of the ambient air. Ambient air naturally has a restricted water vapor content.

The material used for the outer housing of the wash column may in the simplest case be wood. Other materials such as plastic, sheet metal, brickwork and concrete are also possible.

The present application therefore especially also comprises such a process for purifying removal of acrylic acid, methacrylic acid, N-vinylpyrrolidone or p-xylene crystals from their suspension in mother liquor, in which
the suspension is fed to a wash column which has a metal wall which encloses a process chamber,
mother liquor is released from the process chamber while retaining the crystals to form a crystal bed in the process chamber from the suspension conducted into the process chamber,
the crystal bed is conveyed within the process chamber,
at least one force other than gravity acts in the process chamber in the conveying direction of the crystal bed and conveys the crystal bed within the process chamber,
pure melt which consists of molten crystals which have been removed in a purifying manner by the process claimed is conducted within the process chamber in countercurrent to the crystal bed such that a wash front which divides the crystal bed into a mother liquor zone and into a pure melt zone forms in the crystal bed, and
a specific heat flow flows through the metal wall of the wash column into the process chamber of the wash column,
wherein
the metal wall of the wash column which encloses the process chamber is itself enclosed by a shell of a thermal insulation material, with the proviso that
the shell of the thermal insulation material has a water vapor barrier (a water vapor barrier layer),
the wash column enclosed (enveloped) by the thermal insulation material is housed in an outer housing filled with (water vapor-comprising) ambient air and permeable to ambient air,
the temperature of the ambient air present in the outer housing is adjusted (to a value) such that a specific heat flow of >0.1 W/m$^2$ and <10 W/m$^2$ flows into the process chamber through the metal wall of the wash column, and
the dew point temperature plane for the ambient air, coming (viewed) from the direction facing away from the process chamber of the wash column, is beyond the water vapor barrier (beyond the water vapor barrier layer).

The aforementioned specific heat flow is preferably from $\geqq 1$ (or $\geqq 2$) to $\leqq 9$ W/m$^2$, advantageously $\geqq 3$ and $\leqq 8$ W/m$^2$ and most preferably from $\geqq 4$ to $\leqq 7$ W/m$^2$.

Normally, the aforementioned specific heat flow along (in the region of) the mother liquor zone is greater than along (in the region of) the pure melt zone.

The thermal insulation material of the shell preferably consists of a core thermal insulation material (whose thermal conductivity λ (W/m·K) is ≦0.3 W/m·K, preferably ≦0.1 W/m·K, more preferably ≦0.08 W/m·K, even more preferably ≦0.06 and in many cases even ≦0.04 or ≦0.02 or ≦0.01 W/m·K, but generally ≦0.001 W/m·K, frequently even ≧0.002 W/m·K) and of a water vapor barrier layer applied to it (whose thickness is generally from 0.01 to 2 mm). The core thermal insulation materials include all materials mentioned in this document whose λ value satisfies the aforementioned profile of requirements.

Useful materials for the water vapor barrier layer are especially those materials (in particular all of those mentioned in this document) whose μ number is ≧5000, preferably ≧10000 and more preferably ≧15000, even better ≧50000, or ≧100000, or ≧1000000 or ≧10000000.

The sd value of the water vapor barrier layer is favorably ≧500 m, preferably ≧1000 m, more preferably ≧1500 m and most preferably ≧30000 m.

Polyethylene and metal (e.g. aluminum) composite films are particularly suitable as water vapor barrier layers. Especially those of EP-A 1 090 969 and of DE 299 17 320 U1 and those detailed in the prior art acknowledged in the aforementioned documents are useful for the process according to the invention.

In order to protect the wash column enclosed with the thermal insulation material having a water vapor barrier layer additionally from mechanical effects which might breach the water vapor barrier (the water vapor barrier layer) (which would eliminate the water vapor barrier action), it is also appropriate in accordance with the invention to jacket the wash column enclosed by a thermal insulation material having a water vapor barrier additionally with a metal sheet. Suitable metal sheets for this purpose include steel sheets (e.g. stainless steel sheets), which may be, for example, from 0.1 to 2 mm thick, preferably from 0.5 mm to 1 mm thick.

Appropriately from an application point of view, the steel sheet has, on both sides, as corrosion protection, an Al-zinc coating (for example in an amount of 175 g/m² per side). Corresponding steel sheets are commercially available. Metal sheets very particularly suitable in accordance with the invention for this purpose are the Galvalumes® from Thyssen Krupp, especially the sheet sold under the name DX51D+ AZ185A.

Galvalumes are steel sheets which have been upgraded by melt dipping and have, on both sides, an aluminum-zinc alloy coating which comprises approx. 55% by weight of aluminum, approx. 43.4% by weight of zinc and approx. 1.6% by weight of Si. The steel sheets may, for example, be a DIN material of numbers 1.0226 or 1.215. The steel sheet is preferably a cold-rolled steel sheet.

The outer sheet metal jacket of the wash column enclosed in a water-vapor-tight manner is normally mounted at a distance of about 10 mm from the outer surface of the shell having the water vapor barrier. The intermediate space is normally occupied by ambient air, from which the outer sheet metal jacket is not secluded in an airtight manner. The individual sheet metal elements of the outer sheet metal jacket are, appropriately from an application point of view, bonded to one another with the aid of sheet metal screws. On the side of the outer sheet metal jacket facing the wash column, the sheet metal screws appropriately end in a protective Styropor belt.

Preference is given in accordance with the invention to employing wash columns with a cylindrical process chamber. Their diameter is generally ≧25 cm, usually ≧50 cm. Typically, the diameter will not exceed 3 m. Appropriate diameters from an application point of view are from 1 m to 2 m.

Apart from this, preference is given in accordance with the invention to employing hydraulic wash columns as described in DE-A 101 56 016, DE-A 100 17 903, DE-A 100 36 880 and DE-A 100 36 881.

The process according to the invention is favorable, inter alia, in the case of wash columns whose removal performance is ≧0.5 metric ton/h or ≧1 metric ton/h. In general, the removal performance will not be more than 30 metric tons/h. Typical values are from 2 to 20 metric tons/h.

In FIGS. 1 to 4 of this document, the numbers are defined as follows:

1: Suspension
2: Residual melt (mother liquor)
3: Product (molten pure crystals)
4: Impure residual melt
5: Moving crystal bed
6: Wash liquid (melt)
7: Wash column
8: Suspension pump
9: Heat transfer for melting the crystals
10: Control valve for setting the quantitative ratio of wash liquid (melt)/product
11: Circulation pump of the melt circuit
12: Melt circuit
13: Stirrer
14: Filter tube
15: Filter
16: Rotating blade for resuspending the washed crystals
17: Oscillating piston with filtering end face and residual melt outlet
18: Pitched-blade rotor for the transport of the crystal bed
19: Cylindrical displacer According to the invention, it is also possible to use pulsed wash columns or to operate the wash column with pulsating streams, as described by EP-A 097 405.

The process according to the invention is suitable especially for purifying removal of acrylic acid, methacrylic acid, N-vinylpyrrolidone or p-xylene crystals as target product crystals from their suspension in mother liquor, which are obtainable, for example, by suspension crystallization of crude melts of the particular target product comprising impurities, which comprise ≧70% by weight, or ≧80% by weight, or ≧90% by weight, or ≧95% by weight, or ≧98% by weight of the particular target product (acrylic acid, methacrylic acid, N-vinylpyrrolidone or p-xylene).

The process according to the invention is very particularly favorable for purifying removal of acrylic acid crystals from their suspension in contaminated acrylic acid melts, as described in WO 01/77056.

These are suspensions which are obtainable, for example, by suspension crystallization of crude acrylic acids which comprise, for example,

| | |
|---|---|
| ≧70% by weight of | acrylic acid, |
| up to 15% by weight of | acetic acid, |
| up to 5% by weight of | propionic acid, |
| up to 5% by weight of | low molecular weight aldehydes, |
| up to 3% by weight of | polymerization inhibitors, and |
| up to 5% by weight of | acrylic acid oligomers (Michael adducts); |

(these crude acrylic acids frequently additionally comprise up to 20% by weight of water)
or -continued

| | |
|---|---|
| ≧90% by weight of | acrylic acid, |
| from ≧100 ppm by weight to ≦5% by weight of | acetic acid, |
| from ≧10 ppm by weight to ≦2% by weight of | propionic acid, |
| up to 2% by weight of | low molecular weight aldehydes, |
| up to 2% by weight of | polymerization inhibitors, and |
| from 0 to 3% by weight of | acrylic acid oligomers (Michael adducts) |

(these crude acrylic acids frequently additionally comprise up to 9.5% by weight of water).

The process according to the invention is, though, also suitable in the case of the p-xylene crystal suspensions of EP-A 097 405.

Figure 5:
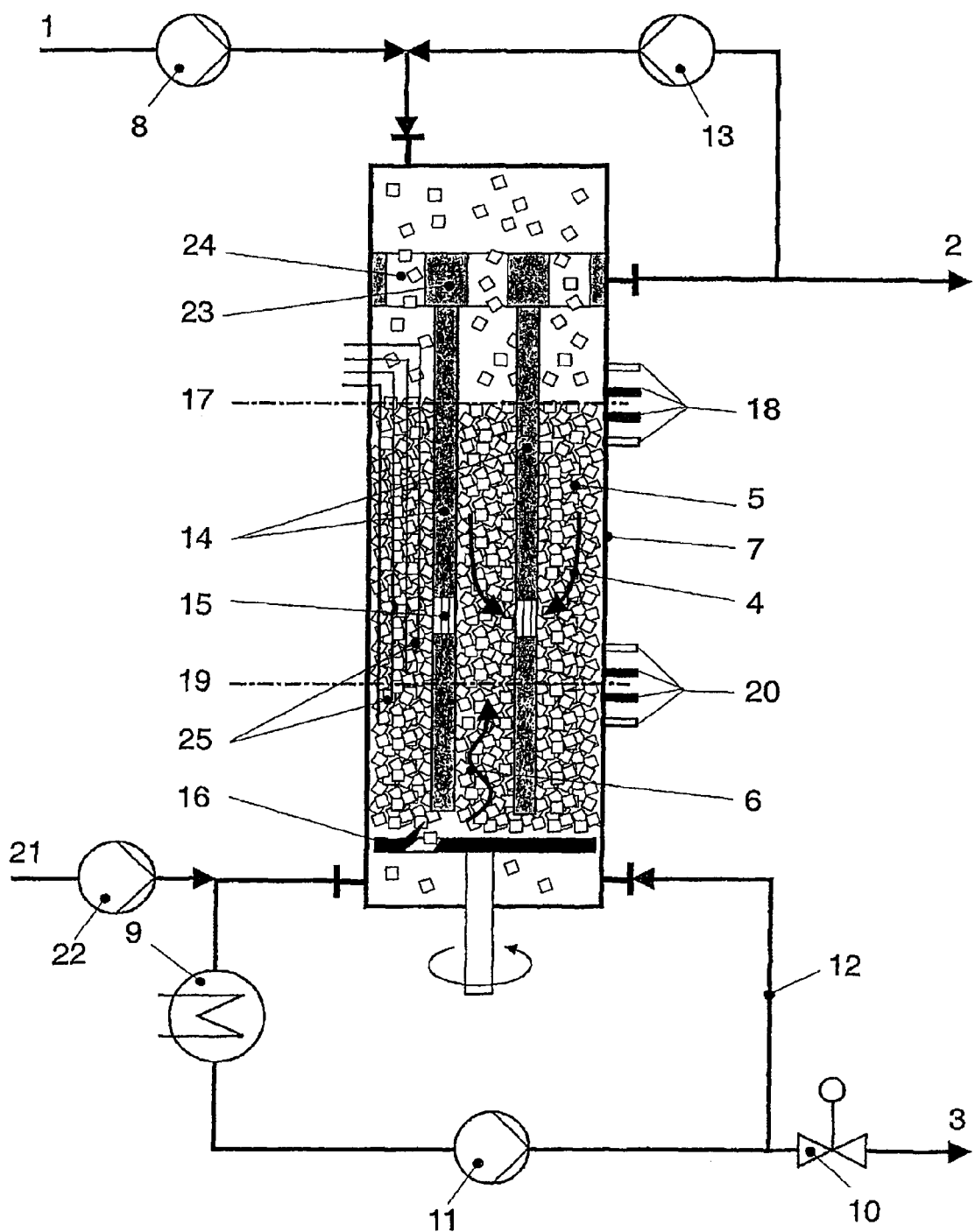
FIG. 5: A schematic of the structure of a hydraulic wash column according to the invention.

The FIG. 5 appended to this document shows a schematic of the structure of a hydraulic wash column suitable in a typical manner for the process according to the invention. It is illustrated in detail below using the example of a purifying removal of acrylic acid crystals.

The suspension (1) of acrylic acid crystals in mother liquor drawn off from the suspension crystallizer is fed into the wash column (7) under superatmospheric pressure by means of a pump (8) and/or by means of hydrostatic head. Arranged in the upper part of the wash column is a fluid register which fulfills two functions. The suspension is distributed over the cross section of the wash column through passage orifices (24) from the upper to the lower part of the column. The continuous interior of the fluid register (23) serves as the collector for the liquids removed (mother liquor and wash liquid (2)). At the bottom of the fluid register are mounted drainage tubes (14) (they have a constant cross section within the concentration zone; this is the zone up to the first filter from the point of view of the suspension feed), which are connected to the interior (23). The drainage tubes are each provided at a defined height with at least one conventional filter (15), through which the mother liquor (4) is removed from the wash column (the mother liquor may be under standard pressure, elevated pressure or under reduced pressure). It forms a compact crystal bed (5). The crystal bed is transported by the force resulting from the hydraulic flow pressure drop of the mother liquor past the filters into the wash zone below the filters. The recycling of a portion of the mother liquor into the column by means of the control flow pump (13) enables the regulation of this transport force. Variations in the crystal content in the suspension supplied or changes in the crystal size distribution, which significantly influences the flow pressure drop, can be compensated for as a result. It is possible to recognise such deviations resulting from the change in position of the filtration front (17), which can be determined with optical position detectors (18).

At the lower end of the wash column, the crystals are removed from the crystal bed by means of a rotor blade (16) and resuspended in pure product melt, which can be overinhibited with p-methoxyphenol (MEHQ) as a polymerization inhibitor. This suspension is conducted through a heat exchanger (9) in a melt circuit (12), by means of which the heat required to melt the crystals is introduced by an indirect route. From about 70 to 80% by weight, in favorable cases (for example in the case of pronounced recrystallization) even from >80 to 100% by weight, of the molten crystals are removed from the melt circuit as pure product (3). The amount of pure product withdrawn is adjusted by means of the product control valve (10). The remaining portion of the pure product melt flows, as wash medium (6), against the transport direction of the crystal bed to the filters (15), as a result of which the crystals are washed in countercurrent in the wash zone. The purification of the crystals is based essentially on the displacement and dilution of the mother liquor into the voids of the crystal bed by wash liquid. The dilution effect is based here on mixing in the voids between the crystals through which flow occurs and diffusion in the contact points through which flow does not occur, i.e. of the flow interface layer of the crystals close to the surface.

In steady-state operation, the wash front (19) is established at a defined height in the wash zone. At the height of the wash front, the concentration transition of mother liquor concentration (above the wash front) and pure melt concentration (below the wash front) takes place. To achieve an adequate purifying effect, the wash front (19) has to be positioned at a minimum height above the rotor blade (16). The position (19) is established as a dynamic equilibrium between transported crystal mass flow (5) and opposing wash medium flow (6), and is below the filter. The amount of wash medium results from the amount of pure product removed.

In the case of already comparatively good purity of the crude acrylic acid, the crystallization temperature in the suspension crystallizer is only from 1 to 4° C. below the pure product melting point. When temperature equalization of the cold crystals with the wash melt occurs, there is therefore only a slight degree of recrystallization of the wash melt in the region of the wash front. This limits both the recovery of wash melt through recrystallization and the reduction in the porosity of the crystal bed below the wash front through recrystallization. Such a low crystal bed porosity would reduce both the wash medium demand and recovery by recrystallization.

In the case of good purity of the crude acrylic acid, it is also appropriate to feed the storage stabilizer methoxyphenol (MEHQ) actually into the melt circuit (12) of the wash column. To this end, MEHQ dissolved in pure product is added with a metering pump (22) to the melt circuit at melting temperature to stabilize it.

To ensure stable operation of the hydraulic wash column in the sense of a defined space-time yield and a constantly good cleaning action, it is appropriate to compensate for external disruptive factors such as
 variations in the amount of suspension,
 change in the crystal content in the suspension,
 variation in the crystal size distribution and
 concentration variations in the feed and/or the mother liquor
by the control of
a) the filtration front (FIG. 5, number 17),
b) the specific amount of wash medium (FIG. 5, number 6) and
c) the heat of melting (FIG. 5, number 9).

In addition, the numbers in FIG. 5 are defined as follows:
1=feed of the crystal suspension
2=mother liquor withdrawal
3=pure acrylic acid product
4=internal mother liquor stream
5=moving crystal bed
6=wash melt
7=wash column
8=suspension pump
9=heat transferer for melting the crystals
10=control valve for adjusting the quantitative ratio of wash melt/pure acrylic acid product withdrawal
11=circulation pump of the melt circuit
12=melt circuit
13=control stream pump 14=drainage tube for mother liquor and wash liquid
15=filter
16=rotor blade for resuspending the washed crystals
17=filtration front (upper limit of crystal bed)
18=detection of the filtration front (4 optical reflectance sensors)
19=wash front (concentration transition from pure to impure liquid phase)
20=detection of the wash front (4 optical reflectance sensors)
21=inhibitor solution (MEHQ in pure acrylic acid product)
22=metering pump for the inhibitor solution
23=fluid register: collecting tray for mother liquor and wash liquid
24=fluid register: distributor plate for the crystal suspension
25=detection of the wash front (4 temperature sensors)

Otherwise, the procedure may be as in WO 03/041833.

Example

As a result of fractional condensation of a product gas mixture of a two-stage heterogeneously catalyzed gas phase partial oxidation of propene, 1.5 t per hour of crude acrylic acid of the following composition contents were drawn off in the side draw of a fractional condensation column:

| | |
|---|---|
| acrylic acid | 96.1% by weight |
| acrolein | 446 ppm by weight |
| allyl acrylate | 20 ppm by weight |
| diacrylic acid | 3764 ppm by weight |
| acetic acid | 7460 ppm by weight |
| furfural | 6719 ppm by weight |
| benzaldehyde | 7131 ppm by weight |
| propionic acid | 751 ppm by weight |
| phenothiazine | 91 ppm by weight |
| MEHQ | 247 ppm by weight |
| water | 0.83% by weight |

Continuous addition of 22.5 kg/h of water to the crude acrylic acid increased its water content to 2.3% by weight, and it was then fed to a suspension crystallizer with a temperature of 20° C. The crystallizer used was a cooling-disk crystallizer (from GMF, The Netherlands) with 7 cooling disks of diameter 1.25 m and a capacity of about 2500 l. The coolant conducted through the cooling disks was a water/glycol mixture (70/30% by volume). As the melt was passed through the crystallizer, it was cooled to 8° C., in the course of which about 24% by weight of crystals formed based on the total mass of suspension.

A portion of this suspension was conducted continuously via a rotary piston pump (speed-controlled) to a hydraulic wash column. This wash column had a cylindrical process chamber with internal diameter 263 mm and had a metal wall of stainless steel 1.4571 with wall thickness 5 mm which delimited the process chamber. For the liquid removal, a centrally installed filter tube (of the same stainless steel) with an external diameter of 48 mm (wall thickness=2 mm) was used in the wash column. The length of the process chamber was 1230 mm. The length of the filter tube was 1225 mm. The filter length was 60 mm. The filter was installed after a tube length of 970 mm (measured from the top). The crystals were removed at the lower end of the wash column with a rotating blade (60 rpm). The transport direction was from the top downward.

The crystals removed were resuspended in a melt circuit which was operated at 14° C. (melting point of the crystals removed in a purifying manner). The polymerization inhibitors used were MEHQ and air (by sparging) into the suspension conducted in circulation (278 ppm by weight of MEHQ). By means of a heat exchanger, heat was introduced into the suspension conducted in circulation by an indirect route in order to substantially melt the crystals resuspended therein. The pump used in the melt circuit was a centrifugal pump (1500 rpm) with a double-action slip-ring seal. The working fluid used was a water/glycol mixture (85/15% by volume), which was cooled indirectly with cooling water. In order to obtain better acrylic acid exchange in the region of the slip-ring seal of this pump, a flush line was conducted from the pressure side of the pump to the product chamber surrounding the slip-ring seal and operated open and continuously. The position of the wash front in the column was monitored by a plurality of thermometers installed axially at different heights in the wash column, and controlled by adjusting the amount of pure product drawn off from the melt circuit. The crystal bed height was controlled by means of four optical sensors mounted axially at different heights on the wash column wall and by adjusting the amount of control stream. The control stream pump used was likewise a rotary piston pump (speed-controlled), but it would also have been possible to use a centrifugal pump with a control valve.

With the aid of steel tensioning belts, a cylindrical shell of Styropor whose layer thickness was 50 mm was applied to the outer metal wall of the wash column.

Subsequently, in an overlapping adhesive-bonded manner, Alu-Butyl foil from WeGo Systembaustoffe VTI branch in 67014 Ludwigshafen, was adhesive-bonded to the thermal insulation layer of Styropor.

The wash column thus enveloped was accommodated in an outer housing which had been manufactured from wooden boards and was permeable to the ambient air, and the (ambient) air present between the enveloped wash column and the wood wall was heated with a heater such that the air temperature in the entire housing was in the range from 23° C. to 26° C. (measured at ten representative measurement points). The relative air humidity of the ambient air at these temperatures was approx. 85%.

The wash column was charged with an amount of suspension of 1400 kg/h from the cooling disk crystallizer. The temperature of the suspension was 8° C. An elevated pressure compared to atmospheric of from 2.0 to 2.2 bar was established at the top of the wash column, which varied in a narrow range about the mean value of 2.05 bar. The elevated pressure at the lower end of the column was from 1.8 to 2.0 bar. A control stream pump was used to return an amount of control stream of 1400 kg/h to the wash column in order to adjust the crystal bed height.

The pure product stream of purified acrylic acid drawn off from the melt circuit was from 310 to 340 kg/h (i.e., on average, 325 kg/h). This corresponds to a yield of 96.7% by weight based on the crystal mass flow fed to the wash column with the suspension. The pure product had the following composition contents:

| | |
|---|---|
| acrylic acid | 99.75% by weight |
| acrolein | not detectable |
| allyl acrylate | not detectable |
| acetic acid | 1457 ppm by weight |
| furfural | 3 ppm by weight |
| benzaldehyde | 2 ppm by weight |
| propionic acid | 209 ppm by weight |
| phenothiazine | not detectable |
| MEHQ | 278 ppm by weight |
| water | <0.05% by weight |

The wash front was of satisfactory stability over the entire experiment.

Both for the steady operating state described and in the subsequent time of 14 days, no condensate formation whatsoever was observed. The specific heat flow flowing into the process chamber of the wash column was from 5 to 6 W/m² along the pure melt zone and about 8 W/m² along the mother liquor zone.

COMPARATIVE EXAMPLE

The procedure was as in the example. However, the inventive envelope of the wash column was omitted. Even before the steady operating state had been attained (i.e. approx. 30 minutes after startup), condensate formation was discernible on the outer stainless steel wall of the wash column.

U.S. Provisional Patent Application No. 60/949,056, filed Jul. 11, 2007, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

The invention claimed is:

1. A process for purifying removal of a crystal of acrylic acid, methacrylic acid, N-vinylpyrrolidone or p-xylene from a suspension thereof in mother liquor, comprising:

feeding a suspension including a crystal to a wash column which has a metal wall which encloses a process chamber;

releasing mother liquor from the process chamber while retaining the crystal to form a crystal bed in the process chamber from the suspension conducted into the process chamber;

conveying the crystal bed within the process chamber such that at least one force other than gravity acts in the process chamber in a conveying direction of the crystal bed and conveys the crystal bed within the process chamber;

conducting a pure melt comprising a molten crystal removed in a purifying manner within the process chamber in countercurrent to the crystal bed such that a wash front which divides the crystal bed into a mother liquor zone and into a pure melt zone forms in the crystal bed; and providing a specific heat flow through the metal wall of the wash column into the process chamber of the wash column, wherein the metal wall of the wash column which encloses the process chamber is enclosed by a shell comprising a thermal insulation material, the shell comprising the thermal insulation material has a water vapor barrier whose environment facing away from the process chamber is permeable to the ambient air and whose surface facing away from the process chamber has a temperature which is above the dew point of the ambient air, and the specific heat flow flowing into the process chamber of the wash column through its metal wall is >0.1 W/m² and <10 W/m².

2. A process for purifying removal of a crystal of acrylic acid, methacrylic acid, N-vinylpyrrolidone or p-xylene from a suspension thereof in mother liquor, comprising:

feeding a suspension including a crystal to a wash column which has a metal wall which encloses a process chamber;

releasing mother liquor from the process chamber while retaining the crystal to form a crystal bed in the process chamber from the suspension conducted into the process chamber;

conveying the crystal bed within the process chamber such that at least one force other than gravity acts in the process chamber in a conveying direction of the crystal bed and conveys the crystal bed within the process chamber;

conducting a pure melt comprising a molten crystal removed in a purifying manner within the process chamber in countercurrent to the crystal bed such that a wash front which divides the crystal bed into a mother liquor zone and into a pure melt zone forms in the crystal bed; and providing a specific heat flow through the metal wall of the wash column into the process chamber of the wash column, wherein the metal wall of the wash column which encloses the process chamber is enclosed by a shell comprising a thermal insulation material, the shell comprising the thermal insulation material has a water vapor barrier, the wash column enclosed by the thermal insulation material is housed in an outer housing filled with ambient air and permeable to ambient air, a temperature of the ambient air present in the outer housing is adjusted such that a specific heat flow of >0.1 W/m² and <10 W/m² flows into the process chamber through the metal wall of the wash column, and a dew point temperature plane for the ambient air, viewed from the direction facing away from the process chamber of the wash column, is beyond the water vapor barrier.

3. The process according to claim 1 or 2, wherein the specific heat flow is from $\geq 1$ to $\leq 9$ W/m².

4. The process according to claim 1 or 2, wherein the specific heat flow is from $\geq 2$ to $\leq 8$ W/m².

5. The process according to claim 1 or 2, wherein the thermal conductivity of the thermal insulation material is $\geq 0.001$ W/m·K and $\leq 0.3$ W/m·K.

6. The process according to claim 1 or 2, wherein the thermal conductivity of the thermal insulation material is $\geq 0.002$ W/m·K and $\leq 0.1$ W/m·K.

7. The process according to claim 1 or 2, wherein the water vapor barrier consists of a material whose water vapor diffusion resistance number is $\geq 15000$.

8. The process according to claim 1 or 2, wherein the water vapor barrier consists of a material whose water vapor diffusion resistance number is $\geq 100000$.

9. The process according to claim 1 or 2, wherein the water vapor barrier comprises a metal foil.

10. The process according to claim 1 or 2, wherein the water vapor barrier comprises an aluminum foil.

11. The process according to claim 1 or 2, wherein the thermal insulation material comprises a polystyrene material with an aluminum composite film applied to the polystyrene material as a water vapor barrier.

12. The process according to claim 1 or 2, wherein a temperature difference between the mother liquor zone and the pure melt zone is from 3 to 12° C.

13. The process according to claim 1 or 2, wherein the wash column enclosed by the thermal insulation material is additionally jacketed by a metal sheet not secluded from the ambient air.

* * * * *